United States Patent [19]

Fukada et al.

[11] Patent Number: 4,550,603

[45] Date of Patent: Nov. 5, 1985

[54] ABNORMAL NOISE DETECTOR FOR USE IN THE INSPECTION OF GEAR UNITS

[75] Inventors: Koichi Fukada, Kobe; Hiroshi Sugimoto, Toyonaka, both of Japan

[73] Assignee: Mitsubishi Denki Kabushiki Kaisha, Japan

[21] Appl. No.: 593,836

[22] Filed: Mar. 27, 1984

[30] Foreign Application Priority Data

Mar. 29, 1983 [JP] Japan ................. 58-55602

[51] Int. Cl.⁴ .......................................... G01N 29/00
[52] U.S. Cl. ...................... 73/587; 73/593; 73/659; 73/660
[58] Field of Search ............... 73/587, 593, 659, 660

[56] References Cited

U.S. PATENT DOCUMENTS

| | | | |
|---|---|---|---|
| 1,644,876 | 10/1927 | Domizi | 73/593 |
| 2,340,714 | 2/1944 | Traver et al. | 73/593 |
| 3,699,806 | 10/1972 | Weichbrodt | 73/593 |
| 4,352,293 | 10/1982 | Kurihara et al. | 73/593 |
| 4,429,578 | 2/1984 | Darrel et al. | 73/659 |
| 4,437,163 | 3/1984 | Kurihara et al. | 73/593 |
| 4,488,240 | 12/1984 | Kapadia et al. | 73/660 |
| 4,514,797 | 4/1985 | Begin | 73/660 |

*Primary Examiner*—Howard A. Birmiel
*Attorney, Agent, or Firm*—Leydig, Voit & Mayer

[57] ABSTRACT

An abnormal noise detector for detecting abnormal noises resulting from a marred tooth surface in a gear of a gear unit is disclosed. A first embodiment of a detector comprises a microphone placed in the vicinity of a gear unit to be tested, a bandpass filter for filtering the output of the microphone so as to pass only an integral multiple of the fundamental frequency of noise due to meshing of the gears of the gear unit, a rectifier for rectifying the filtered output from the bandpass filter, a differentiator for differentiating with respect to time the DC output from the rectifier, a waveform shaper for shaping the output from the differentiator into pulses suitable for counting, and a pulse counter for quantifying the pulses in the output from the waveform shaper. A second embodiment comprises a microphone, a digital frequency analyzer, and a data monitoring computer responsive to the digital frequency analyzer for monitoring the output thereof.

3 Claims, 5 Drawing Figures

ABNORMAL NOISE DETECTOR FOR USE IN THE INSPECTION OF GEAR UNITS

BACKGROUND OF THE INVENTION

The present invention relates to an abnormal noise detector for use in the inspection of gear units. More particularly, it relates to an abnormal noise detector which can detect flaws in the surface of the teeth of a gear in a gear unit by detecting the abnormal noises resulting from those flaws.

One of the typical sources of abnormal noise from a gear unit is a gear tooth having a marred surface. When such a gear tooth meshes with the teeth of a second gear, an abnormal noise is produced. If the rate of rotation of the gear with the marred tooth is N revolutions per second, the marred tooth will mesh N times per second and an abnormal noise will be produced at intervals of 1/N seconds.

The abnormal noise can manifest itself in several ways. One is in the form of a momentary variation in the sound pressure level of the noise produced by the meshing of the gear with a marred tooth and a second gear. Of all the different noises produced during the operation of a gear unit, the noise having the greatest sound pressure level is that due to the meshing of the gears. For any two gears in a gear unit, the fundamental frequency of this noise is equal to the rate at which the teeth of the two gears mesh. This fundamental frequency will here be referred to as $f_0$ and is equal to $(N)(N_G)$, where $N_G$ is the number of gears teeth in the gear with the marred tooth surface. As shown in FIG. 1a, which is a graph of the variation over time of the sound pressure level of the noise having the fundamental frequency $f_0$, the abnormal noise produced by a marred gear tooth can manifest itself as peaks in the sound pressure level occurring at intervals of 1/N seconds. The width of each peak is equal to the length of time for which the tooth with the marred surface meshes with the teeth of a second gear, and is thus equal to $1/(N \times N_G)$ seconds $= 1/f_0$. A similar variation in sound pressure level can be observed for noises due to meshing whose frequencies are integral multiples of the fundamental frequency $f_0$.

Another way in which the abnormal noise resulting from a marred gear tooth can manifest itself is in the form of a variation in the fundamental frequency of the noise due to meshing of the gears in the gear unit. In a normal gear, this frequency is always equal to $f_0 = (N)(N_G)$. However, when a marred tooth meshes with a second gear, a slight change in the timing of the gear unit can be produced, and this results in a momentary slight variation alpha in the fundamental frequency, as shown in FIG. 1b. This variation occurs at intervals of 1/N seconds (once per revolution), and the width of each variation in frequency is $1/(N \times N_G)$ seconds, the same as the width of the peaks in sound pressure level illustrated in FIG. 1a.

The conventional method for detecting abnormal noises produced by a gear unit is to employ a microphone and a frequency analyzer. A gear unit to be tested is connected between a drive motor and a load such as a second motor, and the gear unit is driven by the drive motor at various speeds. The noise produced by the gear unit is picked up by the microphone which produces a corresponding electrical output signal, and the output signal of the microphone is then provided to the frequency analyzer as an input signal. The frequency analyzer samples the signal from the microphone for a certain period of time T and produces a sound pressure level spectrum representing the average sound pressure level of each frequency of noise produced by the gear unit during the sampling period T at the given rate of rotation. By comparing the sound pressure level spectrum for a gear unit being tested with a standard sound spectrum for a gear unit operating normally, it is possible to detect certain abnormalities in the sound pressure level spectrum due to flaws in the gear unit being tested.

However, this method of detecting abnormal noises is not appropriate for detecting the abnormal noise phenomena illustrated in FIG. 1a and 1b resulting from a gear tooth with a marred surface. One or both of these phenomena may be produced by a given gear unit, and they may be produced continuously or intermittently, depending on the gear unit. Even if both phenomena are produced by a gear unit, they are not necessarily produced simultaneously. Due to the intermittent nature of these abnormal noise phenomena and their very short pulse widths, i.e. $1/(N \times N_G)$ seconds, they are very difficult to detect and analyze using the conventional method of abnormal noise detection using only a microphone and a frequency analyzer. Namely, if the sampling period T of the frequency analyzer is very short, it is easy for the abnormal noise phenomena to occur outside of the sampling period, due to their intermittent nature. On the other hand, if the sampling period T is made long, the variations in sound pressure level and frequency tend to be averaged out, and it is difficult to ascertain noise abnormalities from the resulting data.

SUMMARY OF THE INVENTION

It is therefore the object of the present invention to provide an abnormal noise detector which can reliably detect the abnormal noise produced by a gear unit having a gear with a marred tooth surface, even if this abnormal noise occurs only intermittently.

An abnormal noise detector according to the present invention is constructed so as to continuously monitor the amplitude of the noise produced by the meshing of the gears of a gear unit being tested. Since monitoring is carried out continuously, there is no chance of abnormal variations being overlooked because of a short sampling period T or being averaged out because of a long sampling period T as in the conventional method using a frequency analyzer.

An abnormal noise detector according to the present invention comprises a microphone placed in the vicinity of a gear unit to be tested and a detecting means responsive to the electrical output signal produced by the microphone for detecting momentary variations in the amplitude of the component of the signal from the microphone having a prescribed frequency, the prescribed frequency being an integral multiple of the normal fundamental frequency $f_0$.

In a first embodiment of an abnormal noise detector according to the present invention, the detecting means comprises an adjustable bandpass filter which passes only that component of the output signal from the microphone having the prescribed frequency, a rectifier which produces a DC output signal having a level proportional to the amplitude of the output from the bandpass filter, a differentiator which produces an output signal the level of which is proportional to the differential with respect to time of the output signal from the rectifier, a waveform shaper which shapes any pulses in the output from the differentiator into a form suitable for counting, and a pulse counter which counts the shaped pulses from the waveform shaper.

In a second embodiment of an abnormal noise detector according to the present invention, the detecting means comprises a digital frequency analyzer responsive to the output signal from the microphone and data monitoring means for detecting abnormalities in the output from the digital frequency analyzer.

DESCRIPTION OF THE PREFERRED EMBODIMENTS

Now, a first preferred embodiment of an abnormal noise detector according to the present invention will be described while referring to FIG. 2 of the attached drawings, which is a block diagram of this embodiment.

Figure 2:
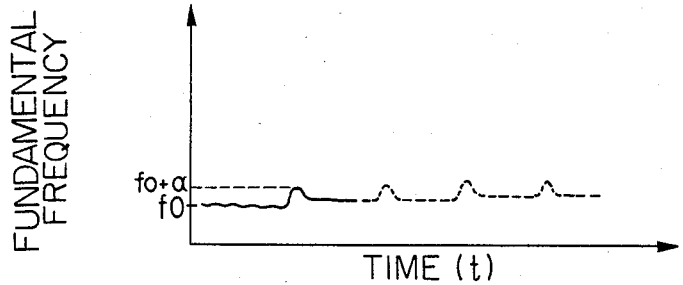
FIG. 2 is a block diagram of a first embodiment of an abnormal noise detector according to the present invention.
Figure 2:
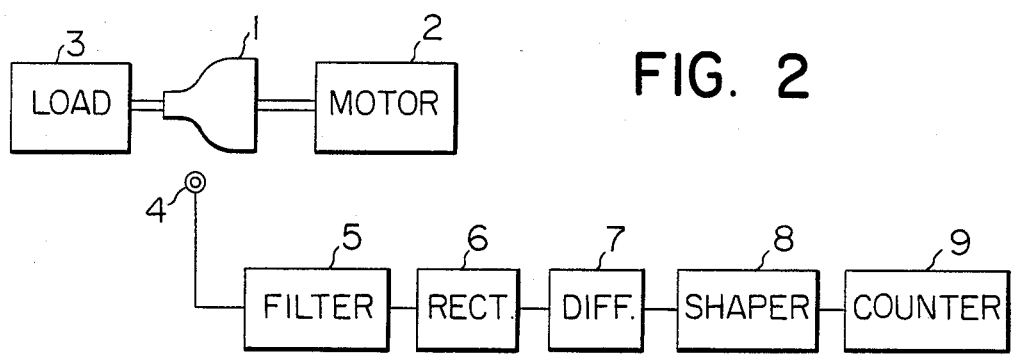

In FIG. 2, element number 1 is a gear unit to be inspected for abnormal noise. Although the gear unit 1 may have any number of gears, it will be assumed here for simplicity that it contains only two gears. The input shaft of the gear unit 1 is connected to a drive motor 2 for driving the gear unit 1, and the output shaft of the gear unit 1 is connected to a load 3 such as a second motor which is in turn driven by the gear unit 1.

The abnormal noise detector according to the present invention comprises elements number 4 through 9. Element number 4 is a microphone placed in the vicinity of the gear unit 1 for picking up the noise produced thereby during testing and producing a corresponding electrical output signal. Elements number 5 through 9 together form means for detecting variations in the amplitude of that component of the output signal from the microphone 4 having a prescribed frequency. Element number 5 is an adjustable bandpass filter electrically connected to the microphone 4 so as to receive the output signal of the microphone 4 as an input signal. Element number 6 is a rectifier which is electrically connected to the bandpass filter 5. The rectifier 6 receives as an input the filtered output signal from the bandpass filter 5 and produces a DC output signal whose voltage is proportional to the amplitude of the output signal from the bandpass filter 5. Element 7 is a differentiator which is electrically connected to the rectifier 6. The differentiator 7 receives as input the output signal from the rectifier 6 and produces an output signal the level of which is proportional to the differential with respect to time of the output signal from the rectifier 6. Element 8 is a waveform shaper electrically connected to the differentiator 7. The waveform shaper 8 receives as input the output signal from the differentiator 7 and produces an output signal consisting of shaped pulses suitable for counting by a pulse counter 9 electrically connected to the wave shaper 8.

When inspecting a gear unit 1 to determine whether it produces abnormal noises due to a gear with a marred tooth surface, the operation of the embodiment shown in FIG. 2 is as follows. The gear unit 1 is driven at some known rate of rotation N by the drive motor 2, and the load 3 is in turn driven by the gear unit 1. The microphone 4 picks up the noise produced by the gear unit 1 and produces an electrical output signal, the amplitude of which is proportional to the sound pressure level of the noise it picks up. The output signal of the microphone 4 is then filtered by the bandpass filter 5. The bandpass filter 5 is previously adjusted so as to pass only a prescribed frequency, i.e. an integral multiple of the normal fundamental frequency $f_o$ corresponding to the present rate of rotation N for the gears in the gear unit 1. Since the rate of rotation N of the motor 2 and the number of teeth in each of the gears of the gear unit 1 are known, the fundamental frequency $f_o$ of the noise due to meshing of the gears in the gear unit 1 can be easily determined. The AC output signal from the bandpass filter 5 is applied as an input signal to the rectifier 6, which rectifies the AC signal to produce a DC output signal the level of which is proportional to the amplitude of the output from the bandpass filter 5. The DC output signal from the rectifier 6 is then provided as an input signal to the differentiator 7, and the differentiator 7 produces an output signal the level of which is proportional to the differential with respect to time of the output signal from the rectifier 6. Any pulses in the output signal of the differentiator 7 are shaped by the waveform shaper 8 into a form suitable for counting, and the pulse counter 9 counts the number of pulses per unit time.

If the gears in the gear unit are without flaws, the sound pressure level of the noise due to meshing of the gears will be constant. Accordingly, the amplitude of the signal which passes through the bandpass filter 5 will be constant, the output of the differentiator 7 will be flat (without pulses), and the pulse counter 9 will produce no output.

However, if the gear unit 1 contains a gear with a marred tooth surface which produces momentary variations in the sound pressure level of the noise having the frequency which passes through the bandpass filter 5 (variations like those illustrated in FIG. 1a), the output signal from the rectifier 6 will contain peaks. These peaks will be differentiated by the differentiator 7 and appear as sharp pulses in the otherwise flat output signal of the differentiator 7. The pulses in the output of the differentiator 7 will be shaped by the waveform shaper 8 into pulses suitable for counting by the pulse counter 9, and the pulse counter 9 will count the number of pulses produced per unit time.

The present embodiment can also detect the situation when a marred tooth surface in the gear unit 1 produces a variation in the fundamental frequency of the noise due to meshing of the gears (the phenomenon illustrated in FIG. 1b). When a momentary variation in the fundamental frequency occurs, the sound pressure level of any noise having a frequency which is an integral multiple of $f_0$ will momentarily change. Since the bandpass filter 5 passes only a signal having a frequency which is an integral multiple of $f_0$, there will occur a momentary variation in the amplitude of the signal from the bandpass filter 5. This results in a momentary variation in the level of the output signal from the rectifier 6. This variation produces a pulse in the output signal from the differentiator 7 which is shaped by the waveform shaper 8 and quantified by the pulse counter 9 in the same manner as described above.

Figure 1:
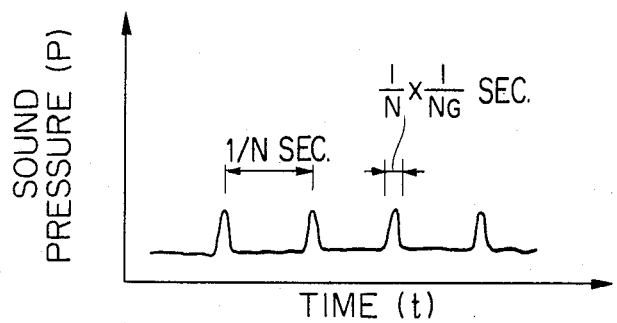
FIG. 1a is a graph of the variation in sound pressure level over time for the noise having a frequency of $f_0$ produced by a gear unit having a gear tooth with a marred surface.
FIG. 1b is a graph of the variation over time of the fundamental frequency of the noise produced by the meshing of the gears of a gear unit having a gear tooth with a marred surface.

Thus, the pulse counter 9 will produce no output when the gear unit 1 is operating normally with no variations in sound pressure level or fundamental frequency, but will produce a non-zero output when either of the phenomena in FIG. 1 occurs. The output of the pulse counter 9 not only indicates the presence of a marred tooth surface, but the magnitude of the output (the number of pulses counted per unit time) can be used to quantify the flaws in the teeth of the gear unit 1.

Figure 3:
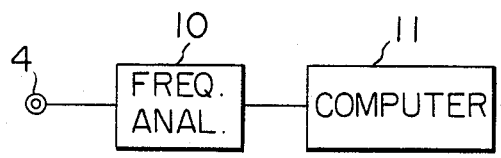
FIG. 3 is a block diagram of a second embodiment of an abnormal noise detector according to the present invention.

FIG. 3 shows a second embodiment of an abnormal noise detector according to the present invention. In this embodiment, the detecting means for detecting variations in the amplitude of that component of the output signal from the microphone having a prescribed frequency comprises a digital frequency analyzer 10 to which the electrical output signal from the microphone 4 is provided as an input signal, and a data monitoring computer 11 which monitors the output of the digital frequency analyzer 10.

Figure 4:
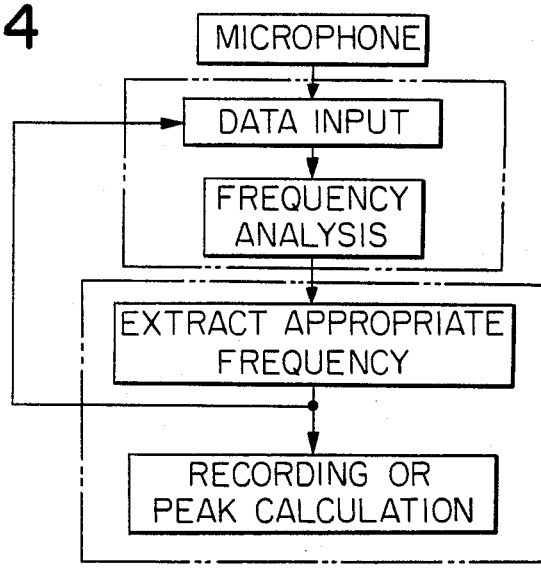
FIG. 4 is a flow chart of the operation of the embodiment illustrated in FIG. 3.

The operation of this second embodiment is illustrated in the operational flow chart in FIG. 4. The electrical output signal from the microphone 4 located in the vicinity of a gear unit being tested is provided to the digital frequency analyzer 10 which performs frequency analysis of this signal and transmits the results of analysis to the data monitoring computer 11. The data monitoring computer 11 can automatically detect flaws in the gear unit being tested by distinguishing the results of analysis of the digital frequency analyzer 10 from the fundamental frequency of noise $f_0$ due to meshing of the gears in the gear unit.

Although the above embodiments have been described for use with a gear unit having only 2 gears, the present invention can be applied equally as well to the testing of a gear unit having 3 or more gears.

What is claimed is:

1. An abnormal noise detector for the inspection of gear units having gears, two of which mesh and produce noise of a normal fundamental frequency which is a function of the rate at which the teeth of said two gears mesh, comprising:
   a microphone placed in the vicinity of a gear unit to be tested; and
   detecting means responsive to an electrical output signal from said microphone for continuously detecting momentary variations in the amplitude of the component of said signal having a prescribed frequency which is an integral multiple of said normal fundamental frequency.

2. An abnormal noise detector as claimed in claim 1 wherein said detecting means comprises:
   filtering means responsive to said signal from said microphone for producing an electrical output signal containing only that component of said output signal from said microphone having said prescribed frequency;
   rectifying means responsive to said filtering means for producing a DC output signal the level of which is proportional to the amplitude of the filtered output signal from said filtering means;
   differentiating means responsive to said rectifying means for producing an electrical output signal the level of which is proportional to the differential with respect to time of said output signal from said rectifying means;
   waveform shaping means for shaping the output signal from said differentiating means into pulses suitable for counting; and
   pulse counting means responsive to the shaped output signal from said waveform shaping means for counting the pulses in said shaped output signal.

3. An abnormal noise detector as claimed in claim 1 wherein said detecting means comprises:
   a digital frequency analyzer electrically connected to said microphone so as to receive the output signal from said microphone as an input signal; and
   data monitoring means responsive to the output of said digital frequency analyzer for determining said amplitude variations representing noise abnormalities reflected in the output of said digital frequency analyzer.

* * * * *